US010272221B2

(12) United States Patent
Foote

(10) Patent No.: US 10,272,221 B2
(45) Date of Patent: Apr. 30, 2019

(54) HUMIDIFIER UNIT

(71) Applicant: Roger Foote, New South Wales (AU)

(72) Inventor: Roger Foote, New South Wales (AU)

(*) Notice: Subject to any disclaimer, the term of this patent is extended or adjusted under 35 U.S.C. 154(b) by 0 days.

(21) Appl. No.: 15/531,912

(22) PCT Filed: May 31, 2016

(86) PCT No.: PCT/AU2016/050428
§ 371 (c)(1),
(2) Date: May 31, 2017

(87) PCT Pub. No.: WO2016/191806
PCT Pub. Date: Dec. 8, 2016

(65) Prior Publication Data
US 2017/0319811 A1    Nov. 9, 2017

(30) Foreign Application Priority Data

Jun. 2, 2015 (AU) .................. 2015902098

(51) Int. Cl.
*F24F 6/02* (2006.01)
*F24F 6/10* (2006.01)
(Continued)

(52) U.S. Cl.
CPC ........ *A61M 16/16* (2013.01); *A61M 16/0066* (2013.01); *A61M 16/109* (2014.02);
(Continued)

(58) Field of Classification Search
CPC .. A61M 16/16; A61M 16/109; A61M 16/142; A61M 16/0066;
(Continued)

(56) References Cited

U.S. PATENT DOCUMENTS

| 4,910,384 A | * | 3/1990 | Silver | A61M 16/16 128/203.17 |
| 6,050,260 A | * | 4/2000 | Daniell | A61M 16/1075 128/203.12 |

(Continued)

FOREIGN PATENT DOCUMENTS

| GB | 915095 | 1/1963 |
| GB | 2173107 | 10/1986 |
| WO | 2015135040 | 9/2015 |

OTHER PUBLICATIONS

Patent Examination Report No. 1, Australia Patent Application No. 2016203593, dated Jun. 5, 2016. (4 pages).
Patent Examination Report No. 2, Australia Patent Application No. 2016203593, dated Jul. 5, 2016. (3 pages).

*Primary Examiner* — Gregory A Anderson
*Assistant Examiner* — Jonathan S Paciorek
(74) *Attorney, Agent, or Firm* — Shutts & Bowen LLP

(57) ABSTRACT

A low cost medical humidifier for adding moisture to a patient air flow is disclosed. The humidifier comprises a water reservoir, a disposable evaporative wick containing a heater, a lid containing electrical contacts to engage the heater in the wick and airway connections. The wick heater comprises a PET film with aluminum tracks and a cover layer of PTC resistive ink. The heater is covered with paper to provide a water pathway via capillary flow. There is a capillary path from the water reservoir to the wick. The wick and heater are manufactured with printing and calendaring processes in reel to reel processes.

11 Claims, 4 Drawing Sheets

(51) Int. Cl.
  *A61M 16/00* (2006.01)
  *A61M 16/10* (2006.01)
  *A61M 16/14* (2006.01)
  *A61M 16/16* (2006.01)

(52) U.S. Cl.
  CPC ............ *A61M 16/142* (2014.02); *F24F 6/02* (2013.01); *F24F 6/10* (2013.01); *A61M 16/107* (2014.02); *A61M 16/161* (2014.02); *A61M 2205/3368* (2013.01); *A61M 2205/3653* (2013.01)

(58) Field of Classification Search
  CPC ........ A61M 2205/3653; A61M 16/107; A61M 16/161; A61M 2205/3368; F24F 6/02; F24F 6/10
  See application file for complete search history.

(56) References Cited

U.S. PATENT DOCUMENTS

| | | | |
|---|---|---|---|
| 6,394,084 B1* | 5/2002 | Nitta | A61M 16/16 128/201.13 |
| 8,459,259 B2* | 6/2013 | Klasek | A61M 16/0066 128/203.26 |
| 8,550,075 B2 | 10/2013 | Virr | |
| 2001/0050080 A1* | 12/2001 | Seakins | A61M 16/08 128/203.16 |
| 2006/0081247 A1* | 4/2006 | Britt | A61M 16/16 128/203.16 |
| 2009/0000620 A1 | 1/2009 | Virr | |
| 2009/0320840 A1* | 12/2009 | Klasek | A61M 16/0875 128/203.27 |
| 2010/0022078 A1 | 1/2010 | Rockenberger | |

* cited by examiner

HUMIDIFIER UNIT

CROSS REFERENCE TO RELATED APPLICATIONS

This Non-provisional Application is a 35 U.S.C. Sect. 371 National Stage entry of PCT/AU2016/050428 entitled "MEDICAL HUMIDIFIER", filed May 31, 2016 and claims the benefit of Australian Application No. 2016203593, filed May 30, 2016 which claims the benefit of Australian Application No. 2015902098 filed on Jun. 2, 2015, the entireties of which are incorporated herein by reference.

TECHNICAL FIELD

The present invention relates to the production of humidified air for use with medical devices. In particular, the present technology relates to the humidification of air intended to be inhaled by a patient. However, it will be appreciated that the invention is not limited to this field of use.

BACKGROUND OF THE INVENTION

The following discussion of the prior art is provided to place the invention in an appropriate technical context and enable the advantages of it to be more fully understood. It will be appreciated, however, that any discussion of the prior art throughout the specification should not be considered as an express or implied admission that such prior art is widely known or forms part of the common general knowledge in the field.

The respiratory system of a healthy body facilitates gas exchange. The nose and mouth form the entrance to the airways of a patient, with the trachea and bronchi being the conducting airways to take the air to the alveolated region of the lungs where the gas exchange takes place. See for example "Respiratory Physiology", by John B. West, Lippincott Williams & Wilkins, 9th edition published 2011.

For example, a respiratory pressure therapy (RPT) device delivers pressurized air to a patient's airway, acting as a splint to keep the airways open, allowing the patient to breathe normally when asleep. The pressurized air is delivered in quantities beyond that required for respiration, with the excess flow allowed to leak out a mask vent so that therapeutic pressure is maintained. RPT is used to treat sleep apnoea and other respiratory disorders. If this flow of air is not humidified, the patient's airways can dry out, causing discomfort to the patient.

The use of a humidifier is intended to produce humidified gas that minimizes drying of the nasal mucosa and increases patient airway comfort. Respiratory humidifiers are available in many forms, and for example may be a standalone device that is coupled to an RPT device via an air conduit; integrated within an RPT device; or be configured so that it is operatively directly coupled to an RPT device.

Humidifiers typically comprise a water tub having a capacity of several hundred milliliters (ml), a heating element for heating the water in the tub, a control to enable the level of humidification to be varied, a gas inlet to receive gas from the RPT device, and a gas outlet adapted to be connected to an air circuit that delivers the humidified gas to the patient interface. In an RPT application, the water tub should contain more than enough water to last for the sleep duration of the patient.

Heated pass-over humidification is one common form used with RPT devices. In such humidifiers, the heating element is typically incorporated in a heater plate which sits under, and is in thermal contact with, the water tub. Heat is transferred from the heater plate to the water tub primarily by conduction. The air flow from the RPT device passes over the heated water in the water tub, resulting in water vapour being taken up by the air flow.

The tub contains the entire volume of water to be used to humidify the flow of air, and receives the flow of air which passes over the water and thereby delivers the humidified flow of air. Such a humidifier configuration presents a number of drawbacks. There is a risk of spillage of the volume of water into the RPT device or to the patient. The entire volume of water must be heated, with a consequent long warm up time and cool down time, of the order of 20 minutes at best. Also, as the tub becomes empty, any contaminants in the water will be adhered as residue in the tub, which will then require cleaning.

Other humidifiers use wick type arrangements, whereby water is drawn through the wick, and the air flows across the surface of the wick, thereby transferring water to the air flow. Water is generally pumped from the reservoir to the wick. A drawback with such wick systems is that the water reservoir is generally at ambient pressure and the water is fed by pump to the wick which is enclosing the pressurized air flow. Thus the pump or water delivery mechanism must act as a valve to prevent loss of air flow and/or pressure, and the pump must deliver a regulated quantity of water to the wick so that flooding does not occur, but still maintain sufficient water in the wick for adequate humidification.

US2009/0000620 (granted as U.S. Pat. No. 8,550,075) discloses a humidifier which includes a water reservoir and a semipermeable membrane on top, to allow diffusion of water vapour. This humidifier requires a complex, specific structure. In particular, it requires a water distribution member comprising an envelope formed by a first compartment wall and a second compartment wall joined together, the water distribution member being supported by a base plate, a heater apparatus supported on the base plate, and (in effect) underneath the water distribution member. Thus, the entire volume of water in the reservoir is heated.

WO2015/135040 discloses a humidifier comprising a reservoir and a pump to provide a flow of water to a humidifier wick, the humidifier wick including a heating element and having a profiled shape so as to enclose at least part of the air flow path through the humidifier.

It is an object of the present invention to provide a more cost effective humidifier and method of humidification.

SUMMARY OF THE INVENTION

In a first broad form, the present invention provides a wick for a humidifier, which includes an internal heating element and which receives water from below via a wicking action. This enables a simple, cost effective humidifier structure in suitable implementations.

According to one aspect, the present invention provides a multilayer humidifier wick, including at least a top layer, a bottom layer, and a heating element intermediate the top and bottom layer, the top and bottom layer being hydrophilic and in communication so that water will pass from the bottom layer to the top layer by a wicking action, such that operatively the bottom layer passes water through the heating element to the top layer, and the heating element increases the temperature of the water in the wick.

According to another aspect, the present invention provides a humidifier for a flow of air, including a reservoir adapted to retain water, a lid, an air inlet and an air outlet, and a wick positioned over the reservoir, the wick including at least a top layer, a bottom layer, and a heating element intermediate the top and bottom layer, the top and bottom layer being hydrophilic and in communication so that water will pass from the bottom layer to the top layer by a wicking action, such that operatively the bottom layer passes water through the heating element to the top layer, and the heating element increases the temperature of the water in the wick, and so that operatively the humidity of a flow of air passing from the inlet to the outlet is increased.

In one form, the humidifier may incorporate a blower for generating the air flow.

According to another aspect, the present invention provides a method of humidifying an air flow, including at least the steps of:
(a) Providing a humidifying chamber with an inlet and an outlet, and a reservoir of water;
(b) Providing a wick positioned above but not in contact with the water, and a transport component extending into the water, so that water travels to the wick using a wicking action;
(c) Heating the wick using an internal heating element, so that the water in the wick is increased in temperature; and
(d) Passing the air flow across an upper surface of the wick, so that the humidity of the air flow is increased.

According to another aspect, the present invention provides a multilayer humidifier wick, including at least a top layer and a heating element below the top layer, the top layer being hydrophilic and in fluid communication with a transport component, the transport component operatively extending into the reservoir, so that in use water travels from the transport component to the top layer using a wicking action, the heating element being operatively adapted to increase the temperature of the water in at least the top layer.

Implementations of the present invention allow for a simple, relatively inexpensive humidifier to be provided. The simplicity and ready manufacturability of the wick, according to suitable implementations of the present invention, allow for easy and cost effective manufacture, and simple assembly and operation.

BRIEF DESCRIPTION OF THE DRAWINGS

Illustrative implementations of the invention will now be described with reference to the accompanying figures, in which.

DETAILED DESCRIPTION OF THE INVENTION

The present invention will be described in more detail with reference to specific implementations. However, it will be appreciated that these are intended as illustrative of the application of the present invention, and not limitative of the scope.

In particular, the present invention will be described primarily in the context of an RPT or CPAP machine, intended to deliver a flow of air to a patient in the context of sleep apnoea and similar conditions. However, the present invention is applicable wherever a flow of air, optionally including medical gases or other materials, is to be delivered to a patient, and humidification is desired. For simplicity, the term 'air' is used in the specification and claims as a general term to include air alone, oxygen, and other medical gases admixed with air or otherwise. The invention should not be considered as limited to any particular field of use, and can be used to humidify an air flow of any desired type.

The present invention may be used in conjunction with a conventional CPAP or RPT apparatus, for examples those commercially available from Resmed Limited, and as described in the references noted above, the contents of which are hereby incorporated by reference.

The present invention may be implemented as a stand-alone system for connection to another apparatus, or as an integrated component within another such apparatus.

Figure 1:
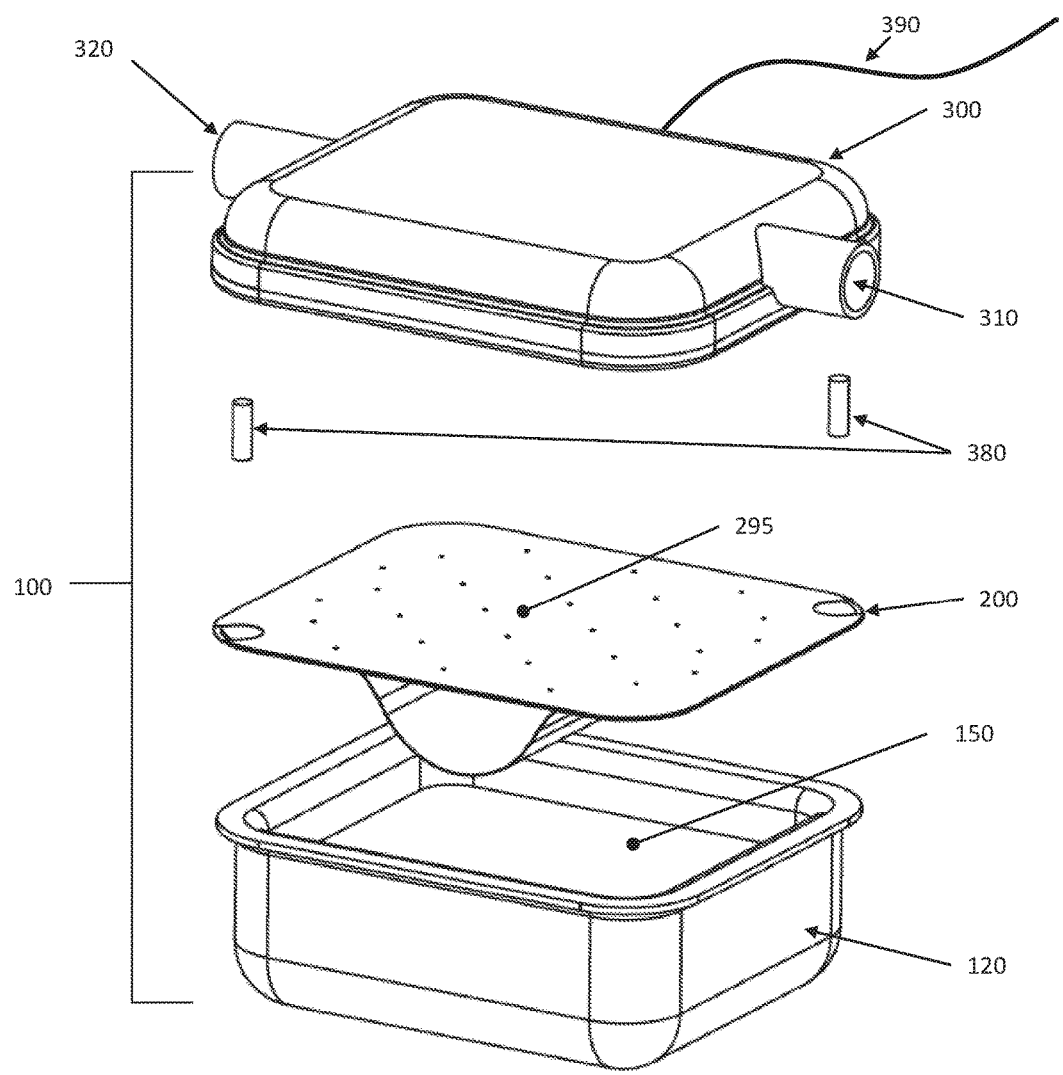
FIG. 1 shows an exploded perspective view of a humidifier according to one implementation of the present invention.

One implementation of the present invention is shown in FIG. 1. This shows a humidifier 100 for increasing the moisture content, or absolute humidity, of a flow of air in relation to the ambient air (air surrounding the patient), before the flow of air is delivered to the entrance of the patient's airways. The humidifier 100 is configured to be coupled directly or indirectly, via an air circuit to a RPT device for receiving the flow of air. The humidifier 100 may be placed upstream or downstream of the RPT device. In one example, the humidifier 100 may deliver a flow of humidified air at approximately 70%-90% relative humidity such as 80% relative humidity and a temperature of approximately 25° C.-30° C. such as 27° C.

The humidifier 100 includes an air inlet 320 to receive a flow of air, and an air outlet 310 to deliver the flow of air with added humidity.

A reservoir 120 is configured to hold a predetermined, maximum volume of water 150 (or other suitable liquids, such as medications, scenting agents or a mixture containing such additives). In one form, reservoir 120 may be configured to hold several hundred milliliters of water 150, for use during at least the length of the patient's sleep in a day.

Reservoir 120 may be formed from any suitable material. It is preferably fabricated from transparent material so that the level of the water 150 is easily observed. In one form reservoir 120 may be made from glass so that it provides a substantial base for the humidifier 100 and is dishwasher safe for easy cleaning. In a preferred form reservoir 120 may be made from borosilicate glass to provide heat resistance to thermal shocks. Of course, in alternative implementations polymers or other suitable materials may be used for the reservoir.

Figure 2:
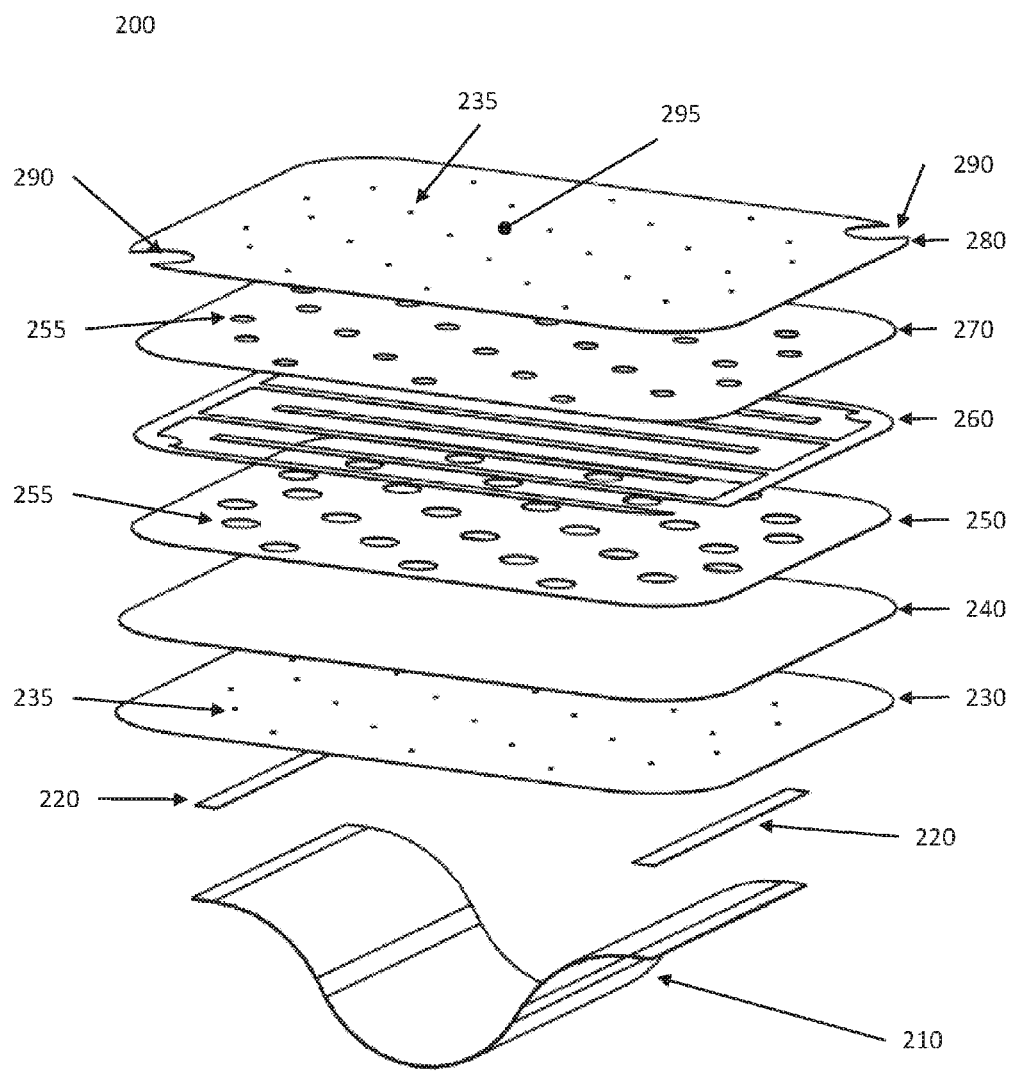
FIG. 2 shows an exploded perspective view of the wick assembly according to one aspect of the present invention.

According to this implementation, and as best seen in FIG. 2, humidifier 100 includes an evaporative wick 200 configured to draw a flow of water 150 from reservoir 120 through wick 200 to the top surface 295. The water feeder loop 210 in this implementation is formed from a high wet strength paper strip adhered by fusible web strips 220 to the bottom surface layer 230 of wick 200.

Water feeder loop 210 is operatively immersed in the water 150 contained in reservoir 120, so that water is draw by capillary action to lower surface 230 of the wick 200 to deliver the flow of water to the top surface 295. Preferably at least the lowest section of the water feeder loop 210 will touch the bottom of the reservoir 120 so that all the water 150 may be drawn to the evaporative wick 200 and evaporated. It will be appreciated that as air is humidified, the level of water 150 in reservoir 120 will reduce, and the water feeder loop 210 needs to remain in contact with water 150.

According to this implementation, the water feeder loop 210 is adhered to the bottom surface of the evaporative wick by the use of a fusible web 220. The fusible web 220 is preferably an open, non-woven web of fine filaments of hot melt adhesive that will adhere both paper elements together but still allow water to pass across the adhesive joint. It is activated by the application of heat to melt the filament and a holding pressure until the filament is below its melting temperature. The melting temperature for the fusible web is preferable above 90° C. and below 150° C.

According to other implementations, the water feeder loop 210 may comprise threaded loops of fibrous twist or braid passing through the wick assembly to contact the water 150 in the reservoir 120. The loop may have a folded, cylindrical, rectangular, conical, or curved shape. It could be formed from, for example, string, rope, braid, woven or non-woven cloth. It could be formed from, for example, paper, cotton, wool, sponge and cellulose fibres, woven, non-woven, twisted or braided natural or synthetic fibres. It could have a profile which is, for example, corrugated, dimpled, perforated, porous, woven, knitted, textured or sintered.

It will be understood that water feeder loop 210 may be formed in alternative implementations from other suitable porous, hydrophilic material, which will provide the desired wicking action. However, paper is presently preferred on the basis of cost and ease of manufacture. Similarly, while the loop is shown as a simple rectangle, other shapes or proportions could be used as desired, consistent with the requiring wicking function, and with specifically the uptake of sufficient water to the wick 200. It may, not be formed as a loop, but for example as a simple tail structure or be formed from several structures.

Wick 200 contains a heater element, formed by a PET film 250 with a patterned layer 260 of conductive material on its top surface, covered in turn by a layer of positive temperature coefficient (PTC) resistive material 270. The thickness of the patterned layer 260 is preferably from 0.2 μm to 20 μm, preferably 1 μm. Preferably, this heater element is fabricated by the high speed printing of a metal precursor onto PET film 250 such as described in US Patent application No. 20100022078, wherein the final metal track is preferably aluminium but may be silver, copper, carbon or other highly conductive material.

The patterned layer 260 forms a set of electrodes for the layer of PTC material 270, and it is the current flowing from one electrode to the other through the PTC layer 270 that provides the heating. As the PTC layer 270 increases in temperature, the resistance increases, thus limiting the heat to a relatively stable temperature. Thus, there is no need for an external or electronic temperature control system: any increase in temperature inherently increases resistance, limiting current in the simple circuit, and so reducing the heat produced in the PTC material. It will be appreciated that this provides a very cost effective and reliable control mechanism for the humidifier.

The preferred controlled temperature value is preferably about 60° C., but may be designed to be limited to any temperature from 40° C. to 80° C. The PTC layer 270 is applied in a uniform film over the entire surface of the patterned layer 260 on PET film 250 with a thickness from 10 μm to 100 μm, preferably 25 μm. The PTC layer 270 in this implementation consists of a polymeric matrix with embedded carbon particles. The polymeric matrix also forms a protective and waterproof cover to the aluminium tracks, thus protecting the tracks from the corrosive environment which may otherwise be found within the evaporative wick 200 from the presence of water and electric potential. By changing the layout of the tracks 260 and thickness of the PTC layer 270, different specific temperatures may be obtained.

It will be appreciated that an implementation of the present invention would be possible, using an electronic control with a sealed conductive heating element.

A suitable PTC material is the commercially available DuPont 7292 carbon based resistor paste, described at dupont.com/content/dam/assets/products-and-services/electronic-electrical-materials/assets/datasheets/prodlib/7292.pdf, the contents of which are hereby incorporated by reference. It will also be understood that whilst a particular PTC material is described, any other suitable PTC material could be used. As will be apparent to those skilled in the art, the details of design will be particular to the materials selected, as their resistance, variation of resistance with heat, and other characteristics will need to be considered in finalising the design in a particular implementation.

The process of forming the metal tracks 260 on the PET layer 250 and covering with PTC 270 material may be performed in a reel to reel (R2R) process. After printing and curing the heater layers, holes 255 are punched in the film through all layers 250, 260 and 270. These holes 255 are designed to allow the flow of water from the bottom layer 230 of the evaporative wick to the top cover 280 of the evaporative wick.

A bottom layer 230 of high wet strength paper is adhered to the bottom surface of the heater assembly 250, 260 and 270 using a fusible web 240. This fusible web 240 is an open, non-woven web of fine filaments of hot melt adhesive that will adhere the paper bottom layer 230 to the heater PET layer 250. It is activated by the application of heat to melt the filament and a holding pressure until the filament is below its melting temperature. The melting temperature for the fusible web is preferable above 90° C. and below 150° C. The size of the bottom layer 230 is larger all round than the heater element, so that there is a width of paper 230 with fusible web 240 protruding beyond the edge of the heater assembly. This protrusion may be from 0.5 mm to 10 mm, preferably from 1 mm to 3 mm, more preferably 2 mm. The bottom layer paper 230 with fusible web 240 will also be exposed through the holes 255 punched into the layers of the heater assembly.

It will be appreciated that although top layer 280 and bottom layer 230 are preferably formed from high wet strength paper, other suitable hydrophilic and water absorbent materials could be used. It is critical that the material exhibit an appropriate level of wicking action in order for the wick 200 to be effective.

A cover layer 280 of high wet strength paper is placed onto the top surface of the heater assembly and bonded to the bottom layer 230 of the evaporative wick 200 through the holes 255 by the exposed fusible web 240 and around the periphery of the evaporative wick by the exposed edge of fusible web 240. The cover layer 280 has cut-outs 290 located in opposing corners to allow contact to be made to the metal tracks 260 through the PTC layer 270.

While the top and bottom layers are shown as generally flat, it will be appreciated that the surface could have an alternative texture, for example corrugated, dimpled, perforated, porous, woven, knitted, or textured.

An illustrative fabrication process for wick 200 will now be described. It will be appreciated that alternative fabrication processes may be employed, and that this represents only one alternative.

The preferred sequence of processing is to start with the PET film 250 and apply by printing the patterned layer 260 as described above. The illustrated implementation preferably uses the disposable heater technology available from Heatron in their DPH Disposable Heater, described at heatron.com/products/details/dph-disposable-heater/, the contents of which are hereby incorporated by reference. Of course, it will be appreciated that suitable alternative heating technologies may be employed.

The PTC layer 270 may then be applied in a uniform thickness over the metal tracks 260 and PET film 250. Holes may then be punched through this subassembly. It will be appreciated that the holes must be positioned to avoid perforating or contacting the conductive tracks 260. It is important in this implementation, as described above, that the PTC layer encases the conductive tracks, to prevent issues with corrosion.

Of course, it will be understood that the holes in the subassembly need not be punched, and could be formed in any suitable way in one or other of the layers, for example integrally formed in the substrate. The holes may be irregular or regular in pattern and shape, and may be of any suitable size, positioning or shape consistent with proper operation and construction of the subassembly.

These processing stages may be carried out using R2R technology which is particularly suitable for high volume processing. The fusible web 240 may be produced by forming the hot melt adhesive filaments directly onto the surface of the bottom layer 230 in a R2R process forming an adhesive coated high wet strength paper. The bonding of the bottom layer 230 to the PET layer 250 and to the top layer 280 may be done using a calendaring process which is also R2R. After the bonding of these layers, small holes 235 are punched through the assembly. These holes have diameters from 0.5 mm to 5 mm, preferably 1 mm to 3 mm, more preferably 1.5 mm and are placed approximately central to the holes 255 punched in the heater subassembly 250, 260 and 270.

Humidifier 100 includes a humidification chamber 360, through which air flows in order to increase the humidity of the flow of air, prior to the air being delivered to the patient. As can be seen from FIG. 1, humidification chamber 360 is formed between the humidifier lid 300 and wick 200. Wick 200 is seated between lid 300 and the reservoir 120.

Humidification chamber 360 preferably contains structures to channel the airflow and increase the turbulence of air flow within the chamber, so that the air entering from inlet 320 does not simply flow in a smooth or laminar way to outlet 310. Turbulent or disrupted airflow will result in an increased rate of evaporation from the wick, and hence more effective humidification of the air flow.

Figure 3:
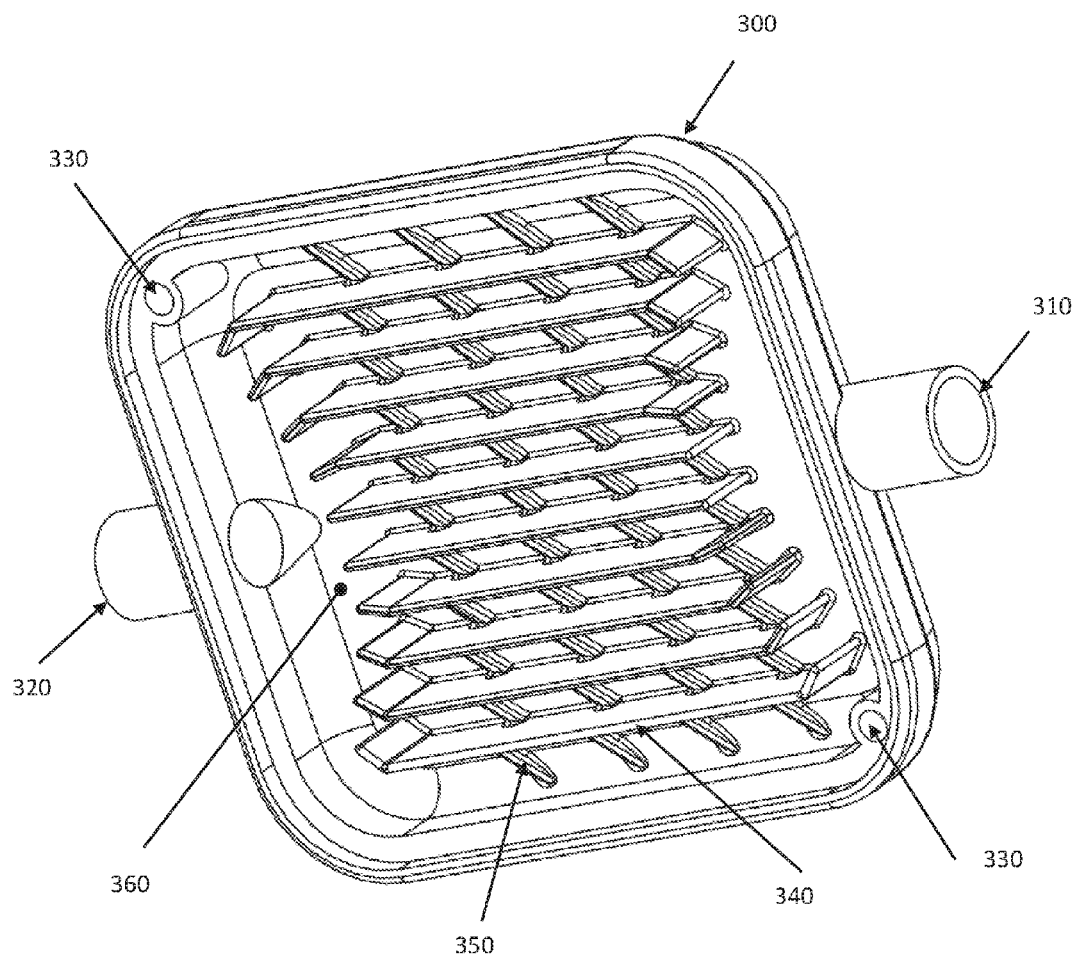
FIG. 3 shows the underside of the humidifier lid according to one aspect of the present invention.
Figure 4:
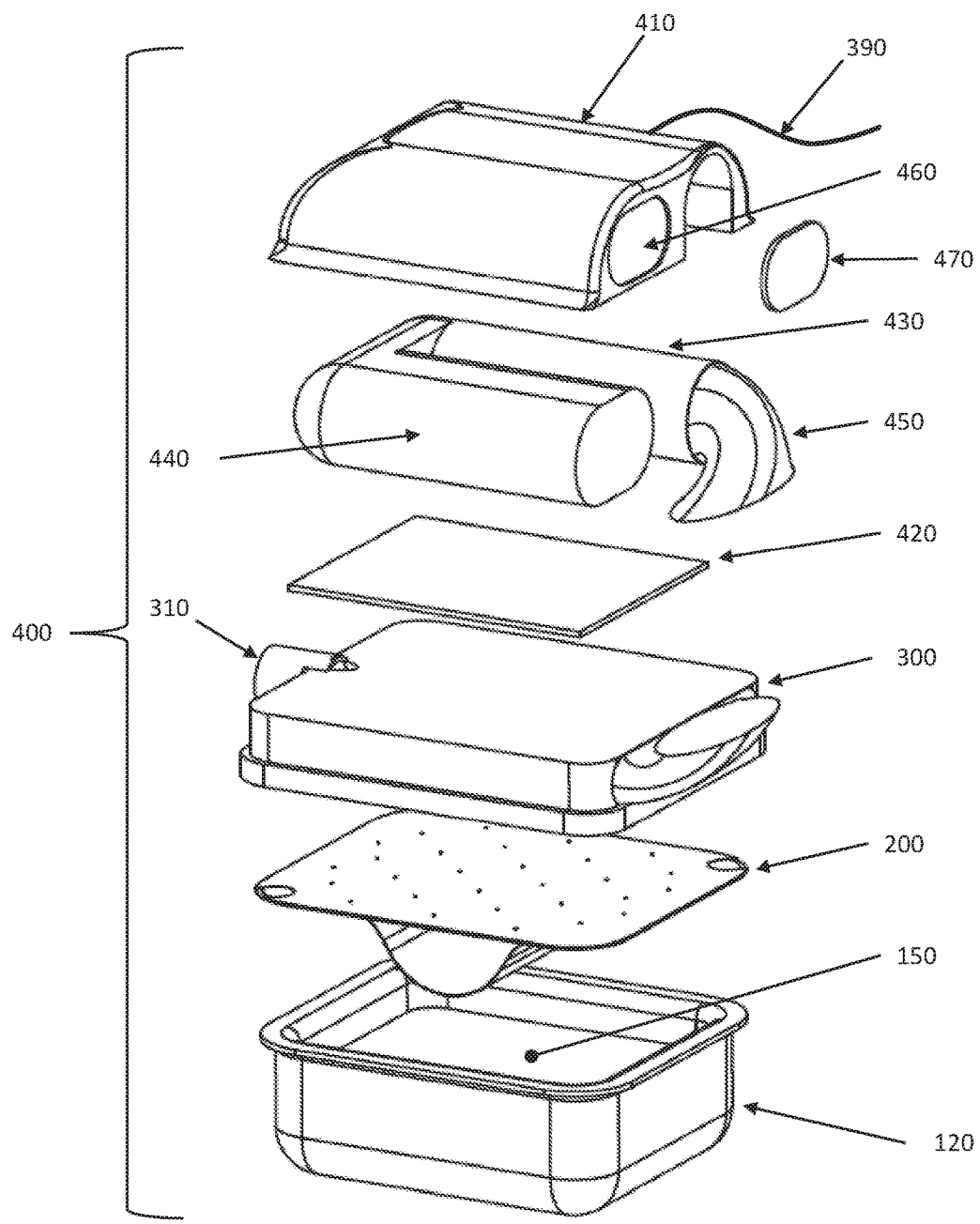
FIG. 4 shows an exploded perspective view of a humidifier according to one aspect of the current technology with a respiratory pressure therapy device housed in the humidifier lid.

Referring to FIG. 3, in this implementation the lid 300 has surface projections in the form of ribs 340, extending from the inner surface of the lid 300 to abut to the surface of the evaporation wick 295. In a preferred form, the ribs 340 may be spaced 10 mm to 30 mm apart, preferably 15 mm to 25 mm apart and more preferably 20 mm apart and the ribs 340 may have a height of 10 mm to 30 mm, preferably 15 mm to 25 mm, more preferably 20 mm.

Lid 300 may also contain turbulators 350 that encourage turbulence of the airflow along the channels formed by the ribs 340. In some implementations, these turbulators 350 may be at an angle of 25° to 65° to the air flow direction, preferably 35° to 55°, and more preferably at 45° to the air flow direction. The height of the turbulators 350 may be 5% to 45% of the height of the ribs 340, preferably 15% to 35% of the height of the ribs 340, more preferably 25% of the height of the ribs 340.

Lid 300 incorporates cavities 330 that locate and hold spring loaded contacts 380. Contacts 380 have flat pads to press onto and provide effective electrical contact with the PTC layer 270. As described above, contact cut-out areas 290 provide a recess to allow for direct electrical contact through the upper layer 280 to the PTC layer 270 for contacts 380. Contacts 380 also connect to the power lead 390 that is connected into the lid 300, preferably by a removable plug arrangement. Thus, contacts 380 facilitate supply power to the heater layers 250, 260, 270.

Ribs 340 also act as stiffening members to reinforce the lid so that pressure may be contained within the sealed assembly without excessive deformation. The ribs 340 also direct the air flow evenly across the evaporative surface 295 to maximize the humidification added to the air flow.

The operation of the illustrative humidifier will now be described. Initially, reservoir 120 is filled with water 150. The wick 200 is placed on top of the reservoir 120 and the lid 300 is placed onto the wick 200 and clamped into place using simple clamps (not shown) to form an airtight seal between the reservoir 120, wick 200 and lid 300. Thus, the risk of accidental water spillage from the reservoir is minimised.

Water 150 is drawn from reservoir 120 by capillary action along water feeder loop 210 through fusible web 220 to the bottom layer 230 of wick 200. The water then spreads out over the entire bottom layer 230 by capillary action. At the holes 255 in the PET film 250 and PTC layer 270, water is drawn by capillary action from bottom layer 220 through fusible web 240 to the top layer 290. There the water spreads out by further capillary action across the entire surface of the top layer 295.

When power is applied to the patterned layer 260, the water contained in wick 200 becomes heated, encouraging evaporation from the surface 295 of top layer 290. Operatively, air is flowing across surface 295, and the air flow takes up evaporated water as it passes through. At the bottom layer 230, the air adjacent quickly reaches a relative humidity of 100% and no further evaporation occurs, because there is no air flow over this surface in the reservoir below the evaporative wick 200. There is no heat directed to the water 150 in the reservoir 120 so it does not become hot. Thus the heat application is efficient with little or no heat being lost. There is no attempt to heat or keep heated the entire reservoir, only the portion in wick 200.

Furthermore, as the water is drawn into the feeder wick 210, residues are not left in the reservoir 120 as a result of heat forced evaporation, and so the reservoir remains clean of such residues. Any impurities in the water 150 are left within the evaporative wick 200 as the water is evaporated.

It is envisaged that wick 200 is disposable and replaced at a regular frequency. The frequency of replacement will vary depending on the quality of water 150 used. Pure water such as distilled water will enable the evaporative wick 200 to last for several months, whereas tap water 150 may require replacement of the evaporative wick 200 within weeks or even days depending on the quality of the tap water. However, it would be possible to construct a wick which was not disposable, from more durable materials, if this was desired.

It will be appreciated that the construction and form of the wick as described in this implementation are such that it is relatively inexpensive to manufacture, and hence having a disposable wick is economical. The design illustrated makes it very easy for a user to replace wick 200, as well as to refill the reservoir as required.

It will be appreciated that a particular size of reservoir with a capacity of a few hundred milliliters is illustrated. It will be appreciated that the principle of the present invention is applicable to any desired size or shape of reservoir. The reservoir could include, for example, openings for filling, or connections to other water storage devices.

In the illustrative example, as the air flow starts, pressure builds up in the humidification chamber 360. Small holes 235 punched through the top layer 280 of wick 200 allow this pressure to pass into the reservoir filled with water and equalize the pressure across the evaporative wick 200. These small holes 235 also prevent splashes from the water surface passing across the evaporative wick 200 into the air stream, so preventing any biohazards in the water 150 passing into the air stream. Furthermore, these small holes 235 act as a deterrent to spill if the humidifier is accidentally tipped over, as the water flow through these holes 235 will be very small, thus minimizing the amount of water lost or spilt to the inlet 320 or outlet 310.

An advantage of implementations of the present invention is that the volume of water held within the evaporative wick 200 is controlled by gravity and surface tension, so it will never become "over full" but will always be saturated while there is water 150 present in the reservoir 120.

Another advantage of implementations of the present invention is that the temperature of the evaporative wick 200 will be controlled by the PTC layer 270, such that it never goes above its specific design temperature. The changing resistance of the PTC layer 270 with temperature controls the power that is consumed by the evaporation of the water from the wick 200. Furthermore, the humidity added to the airflow is controlled by the inability of the air to exceed 100% relative humidity at a specific temperature, so as the air reaches 100% relative humidity at the evaporative wick 200 surface, no more moisture will be added to the airflow.

The evaporative wick may be supplied in various design configurations so that a lower specified temperature may be used for a patient in a warm humid environment with low flow therapy, or a higher specified temperature evaporative wick 200 may be supplied to a patient in a dry cool environment with high flow therapy. As the evaporative wicks 200 are consumable and preferably replaced regularly, an available selection of different specific temperature wicks 200 will allow a patient to achieve a maximum level of comfort in their specific environment.

It will be appreciated that a different sequence of layers in wick 200, or additional layers, may be used to achieve the same function. Further, whilst specific materials are described, the invention may be implemented using alternative materials with appropriate characteristics. The materials may include additional additives or functions. For example, anti-fungal or anti-microbial additives could be used, for example nano-silver, to increase the working life of wick 200.

FIG. 4 illustrates an alternative implementation, in which the lid contains a blower. In this form, there is no inlet from an RTP device, the unit has an integrated blower and takes in ambient air, which is humidified using similar components to the previous example.

The lid 300 in this implementation includes a blower housing 410 that, in this form, includes an inlet filter 470, blower 430, muffler 440, PCB assembly 420. The PCB assembly may include sensors, communications, data storage, display and controls (not illustrated). The form factor of this combination is small as there is only an increase in height of the lid to accommodate blower 430, muffler 440 and PCB assembly 420 containing controls, sensors and communications.

The blower may be a suitably sized electric motor and associated fan. In general, the blower, muffler, and associated electronics may be as used in conventional RPT devices.

The data storage, display and controls may be suitably used with a smart device (such as a smart phone, tablet or the like) connected using wireless communications, for example near field communications or Bluetooth. The smart device may send the data to the cloud, display the current functioning of the RPT device and allow control of the RPT device.

The size of the lid 300 with blower housing 410 as described is such that is easily handled by the patient to remove it from the reservoir 120 to allow removal of the wick 200, filling the reservoir 120 with water 150, and replacement of the wick 200. Wick 200 is as described in relation to the other implementation.

Sensors (not illustrated) located within the blower housing 410 may allow a more sophisticated control of the humidification of the air flow, by sensing the ambient temperature and humidity, and the air flow. On this basis a calculation of the amount of moisture to be added to the air flow is possible, either through direct calculation or by look up tables. The amount of moisture to be added to the air flow is directly related to the amount of energy delivered to the evaporator wick 200, so a target level of humidity may be easily achieved by controlling the delivered energy to the wick 200.

It is also contemplated that an implementation of the present invention could use a heater layer, and a top layer, with the top layer being connected to the water feeder loop (or other wicking structure) either directly or through the heater layer. Thus, the water feeder loop would more directly feed the top layer. If the connection was direct from the loop to the top layer, then the heater layer may not need to be porous. Similarly, suitable constructions of a multilayer wick could allow for passage of water to the top layer without passing through the heater layer.

The heating layer has been described in the context of a planar conductive electrode pattern on a suitable substrate. The substrate has perforations to allow for the wicking passage of water through the substrate. It will be appreciated that heater layer could be made somewhat permeable in other ways, for example including shaped openings, or mesh sections within the substrate. A heater of different construction which allowed wicking passage of water could also be used. The use of alternative heating, for example a coated wire material in which the conductor is sealed from the water, or in which the conductive material will not degrade if exposed to the water, could allow for a porous webbing or similar material to be used for the substrate.

One implementation of the present invention includes the feature that the temperature of the wick may be directly estimated by measuring the resistance of the wick heater 265 when the power is off, and using look up tables to determine the temperature. There is generally an established relationship for the temperature dependant resistance function for the PTC material, made available by the manufacturer in the case of the preferred material noted above. This may be used to determine if water is present in the wick 200 or reservoir 120 as the wick will reach maximum temperature when the water has all evaporated.

Although the illustrated implementations use layers of generally equal size and shape (other than as discussed in relation to the fusible web), it will be appreciated that in alternative implementations different layers could be differently shaped from each other. The holes and orifices need not be circular. The overall shape of the wick 200 is preferably so as to fit neatly and seal within the humidifier as described, but in alternative implementations this may not be the case.

Although the present invention has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

All references, websites and documents referenced in the specification are hereby incorporated by reference into this disclosure.

It is therefore to be understood that numerous modifications may be made to the illustrative embodiments and that other arrangements may be devised without departing from the spirit and scope of the technology.

FIGURE REFERENCE LIST

Air bleed hole 235
Air inlet 460
Blower 430
Blower housing 410
Blower outlet 450
Contact cut-out 290
Evaporative surface 295
Fusible web 240
Humidification chamber 360
Humidifier 100
Inlet 320
Lid 300
Metal tracks 260
Muffler 440
Outlet 310
PCB Assembly 420
PET layer 250
PTC layer 270
Power lead 390
Reservoir 120
Rib 340
RPT device 400
Spring contact 380
Spring contact recess 330
Turbulator 350
Water 150
Water via 255
Wick 200
Wick base 230
Wick cover 280

The invention claimed is:

1. A multilayer humidifier wick, comprising at least a top layer, a bottom layer, and a heating element intermediate the top and bottom layer, the top and bottom layer being hydrophilic and in communication so that water will pass from the bottom layer to the top layer by a wicking action, wherein the wick further comprises a transport component extending down from the bottom layer, so that the transport component is operatively adapted to project into a reservoir of water and transport water from the reservoir to the bottom layer by a wicking action, and the heating element will operatively increase the temperature of the water in the wick.

2. A wick according to claim 1, wherein the transport component is formed from one or more loops.

3. A wick according to claim 2, wherein the top layer at least is generally planar.

4. A wick according to claim 1, wherein operatively water passes through the bottom layer, through the heating element, to the top layer.

5. A wick according to claim 4, wherein the heating element is formed from a substrate, a set of patterned electrodes formed on the substrate, and a conductive layer which electrically connects the electrodes, the conductive layer having a resistance which increases with temperature, such that the conductive layer and electrodes interact to provide a controlled temperature when an electrical current is passed through the electrodes and conductive layer.

6. A humidifier for a flow of air, comprising a reservoir adapted to retain water, a lid, an air inlet and an air outlet, and a wick positioned over the reservoir, the wick comprising at least a top layer, a bottom layer, and a heating element intermediate the top and bottom layer, the top and bottom layer being hydrophilic and in communication so that water will pass from the bottom layer to the top layer by a wicking action, the arrangement being such that operatively the bottom layer passes water through the heating element to the top layer, wherein the wick is positioned so that it is not in direct contact with the water in the reservoir, a transport component extending down from the bottom layer into the reservoir so that operatively the transport component contacts the water and transports water to the bottom layer by a wicking action, and the heating element increases the temperature of the water in the wick, and so that operatively the humidity of a flow of air passing from the air inlet to the air outlet is increased.

7. A humidifier according to claim 6, wherein the wick is operatively positioned over the reservoir so as to provide a seal over the surface of the reservoir.

8. A humidifier according to claim 7, wherein the top layer includes a plurality of small openings, such that air pressure can be equalised across the wick.

9. A humidifier according to claim 7, wherein the air inlet is adapted to receive an air flow generated by another device.

10. A humidifier according to claim 6, wherein the lid includes a blower having a blower inlet and a blower outlet for producing an air flow, and the blower inlet receives ambient air where the air from the blower outlet enters the humidification chamber and the humidifier air outlet deliver humidified air at an elevated pressure.

11. A method of humidifying an air flow, including at least the steps of:
   (a) Providing a humidifying chamber with an inlet and an outlet, and a reservoir of water;
   (b) Providing a wick positioned above but not in contact with the water, and a transport component extending into the water, so that water travels to the wick using a wicking action;

(c) Heating the wick using an internal heating element, so that the water in the wick is increased in temperature; and
(d) Passing the air flow across an upper surface of the wick, so that the humidity of the air flow is increased.

* * * * *